United States Patent [19]

Broude et al.

[11] Patent Number: 5,602,401
[45] Date of Patent: Feb. 11, 1997

[54] DATA PROCESSING SYSTEM AND METHOD FOR A SURFACE INSPECTION APPARATUS

[75] Inventors: Sergey V. Broude, Newton Centre; Nicholas Allen, Bedford; Abdu Boudour, West Newton; Eric Chase, Carlisle; Carl Johnson, Tweksbury; Pascal Miller, North Chelmsford; Jay Ormsby, Salem, all of Mass.

[73] Assignee: QC Optics, Inc., Burlington, Mass.

[21] Appl. No.: 499,933

[22] Filed: Jul. 10, 1995

[51] Int. Cl.$^6$ .................................................. G01N 21/86
[52] U.S. Cl. ................. 250/559.45; 250/559.41; 356/237
[58] Field of Search ............... 250/559.41, 559.48, 250/559.22, 559.45; 356/237, 240, 426–431; 382/118, 31, 65

[56] References Cited

U.S. PATENT DOCUMENTS 33,357   9/1990   Randall ........................ 250/559.46
4,134,684   1/1979   Jette ........................ 250/559.49

*Primary Examiner*—Que T. Le
*Attorney, Agent, or Firm*—Iandiorio & Teska

[57] ABSTRACT

A system for processing particle size and position data for a surface under inspection, the system including an air spindle for rotating and a translation stage for translating the surface with respect to a beam of radiation used to detect particles on the surface; a rotational encoder for dividing the surface into a number N of angular vectors; a counter of counting the number of revolutions of the surface; a processor for collecting particle size and position data at each angular vector during each revolution; first and second FIFO memories having at least N address spaces, each address space allocated for a specific angular vector; and a routine for writing the collected particle size and position data to the first memory and for reading particle size and position data from the second memory and switching memories every M revolutions. The FIFO memories are programmed to store only the greater of stored size data and incoming size data.

14 Claims, 4 Drawing Sheets

DATA PROCESSING SYSTEM AND METHOD FOR A SURFACE INSPECTION APPARATUS

FIELD OF INVENTION

A data processing system and method for a surface inspection apparatus for detecting flaws and particles on a surface such as a photolithographic mask.

BACKGROUND OF INVENTION

Glass photolithographic masks or plates comprising a chrome pattern on a glass or quartz substrate are used in the manufacture of thousands of semi-conductor wafers during a production run using a "stepper" printing machine. Therefore, it is critical that the surface of the mask be free of contaminating particles lest the image of the particles be reproduced on each wafer. Accordingly, the masks are typically inspected before a production run using very precise equipment shown, for example, in U.S. Pat. Nos. 4,943,734; 4,794,264; 4,794,265; and 5,389,794 incorporated herein by reference.

As a mechanical mask holder/spindle assembly spins the mask, the surface of the mask is scanned by a laser beam directed to the surface and the scattering of the laser beam off the surface is analyzed: the scattering off the surface will be different if a flaw or particle is present than if no flaw or particle is present. The scattering can be analyzed to the point where particles or flaw are classified by size. In order to scan for and detect very small particles (e.g. 0.3 microns in diameter), it is very important that the laser beam be focused to form a very small spot size.

Prior surface inspection apparatus utilized various signal processing routines and computer programs to process and analyze the particle data (e.g., size and position) thereby providing the user with a computer generated map which shows the relative size and position of all particles on the mask. The user then uses a microscope to visually inspect any particles of interest. These prior systems, however, were fairly slow. If the photolithographic mask is scanned slowly (e.g. much less than 1800 rpm) and the spot size of a laser beam is quite large (e.g. much larger than 1.7×5.3 micrometers) then the particle size and position data could be processed and analyzed during each scan. These low rates of scanning, however, mean that the inspection of each mask is slow and hence expensive. And, such a large laser beam spot size may fail to accurately detect very small particles.

A faster speed of rotation and a small laser beam spot size, however, makes it impractical to process and analyze the particle data during each scan.

SUMMARY OF INVENTION I

It is therefore an object of this invention to provide a surface inspection system which quickly processes and analyzes particle size and position data on a surface even at very fast rates of scanning.

It is a further object of this invention to provide such a surface inspection system which quickly processes and analyzes particle size and position data even when the laser beam spot size on the surface is very small.

It is a further object of this invention to provide a very fast size and position data processing system for, and a methodology of, processing size and position data in a surface inspection apparatus.

It is a further object of this invention to provide such a data processing system which does not process duplicative data thereby saving processing time and which allows data writing and data reading operations to take place simultaneously thereby further reducing processing time.

It is a further object of this invention to provide such a data processing system and methodology which quickly processes particle size and position data as the surface is scanned at great speed and which facilitates data processing even if the laser beam spot size and trace pattern is very small.

This invention results from the realization that although a laser beam can be focused to inspect a surface for very small particles in a very tight spiral pattern (e.g., 3 microns between successive beam traces), the final required map resolution is much larger (e.g., a 15×15 micron square) so there is no need to permanently record the size data for each particle during each revolution of the surface and furthermore that if the size data of a particular particle is decreasing between revolutions, there is no need to store this extraneous information thereby reducing computing time and increasing the speed of inspection. This invention results from the further realization that if two temporary memories are used to store size and position data, one memory can record size and position data during a number M of scans while the size and position data is transferred from the other memory to permanent memory, and then the record and transmit operations can be alternated between the two memories every M scans of the surface under inspection.

This invention features and may, depending on the specific implementation, comprise, include, consist essentially of, or consist of a surface inspection system. There is a laser beam source; means for focusing a laser beam from the source onto the surface; means for rotating and translating the surface with respect to the means for focusing to trace a spiral pattern with the laser beam on the surface; detection means for detecting scattering of the laser beam from the surface; and means, responsive to the detection means, for calculating the size of any detected particles on the surface and for determining the position of the detected particles on the surface. Also featured are memory means for storing the size and position data of any detected particles; and means, responsive to the memory means, for recording the size and position data of any detected particles on each revolution but transferring the stored data only once per M revolutions (e.g. five). The system further includes means for updating the memory means each revolution for M revolutions only if the incoming size data for a detected particle is larger than the stored size data for that particle. This saves processing time and storage space since superfluous size data is never stored or analyzed.

The memory means typically includes two FIFO memories, one being read from while the second is written to. There are means for switching between the two memories every M revolutions to allow data analysis to take place simultaneously with data acquisition. The FIFO memories are programmed to receive data only if the incoming size data for an address space is greater than the size data stored in that address space.

Therefore, this invention features a data processing system for a surface inspection apparatus which analyzes flaws by size and position on a surface, the data processing system comprising: means for obtaining flaw size and position data from the surface inspection apparatus; first and second memories; means for writing size data to one memory while reading size data from the second memory and switching memories every M revolutions of the surface; and means for replacing a stored size datum for a given position in one of said memories during each revolution for M revolutions with an incoming size datum only if the incoming size datum is greater than the stored size datum.

More generically, this invention features a data processing system comprising: means for counting; means for obtaining data; first and second memories; means for writing data to the first memory while reading data from the second memory and switching memories after every M counts; and means for replacing previously stored data in an address space of one of the first and second memories with incoming data only if the incoming data meets a preselected criteria. The data is typically size and position data and the preselected criteria is typically that the incoming size data must be greater than the stored size data.

More specifically, this invention relates to a system for processing particle size and position data for a surface under inspection. This system comprises means for rotating and translating a surface with respect to a beam of radiation used to detect particles on the surface; means for dividing the surface into a number N of angular vectors; means for counting the number of revolutions of the surface; means for collecting particle size and position data at each angular vector during each revolution; first and second memories having at least N address spaces, each address space allocated for a specific angular vector; means for writing the collected particle size and position data to the first memory and for reading particle size and position data from the second memory and switching memories every M revolutions; and means for storing in each address space of the memories the greater of stored size data and incoming size data.

This invention also features a data processing method for a surface inspection apparatus which analyzes flaws by size and position on a surface, the data processing method comprising: obtaining flaw size and position data from the surface inspection apparatus; writing size data to one memory while reading size data from a second memory and switching memories every M revolutions of the surface; and replacing a stored size datum for a given position in a memory during each revolution for M revolutions with an incoming size datum only if the incoming size datum is greater than the stored size datum.

In general, the method involves obtaining flaw size and position data; writing the data to one memory while reading the data from a second memory and switching memories after every M counts; and replacing previously stored data in an address space of a memory with incoming data only if the incoming data meets a preselected criteria. The preselected criteria is usually that the incoming data must be greater than the stored data.

More specifically, the invention features a method of processing particle size and position data of particles detected on a surface under inspection, the method comprising: rotating and translating a surface with respect to a beam of radiation used to detect particles on the surface; dividing the surface into a number N of angular vectors; counting the number of revolutions of the surface; collecting flaw size and position data at each angular vector during each revolution; establishing first and second memories each having at least N address spaces, each address space allocated for a specific angular vector; writing the collected particle size and position data to the first memory and reading particle size and position data from the second memory and switching memories every M revolutions; and programming the memories to store in each the address space the greater of previously stored size data and incoming size data.

DISCLOSURE OF PREFERRED EMBODIMENT

Other objects, features and advantages will occur to those skilled in the art from the following description of a preferred embodiment and the accompanying drawings, in which:

DETAILED DESCRIPTION OF THE INVENTION

Figure 1:
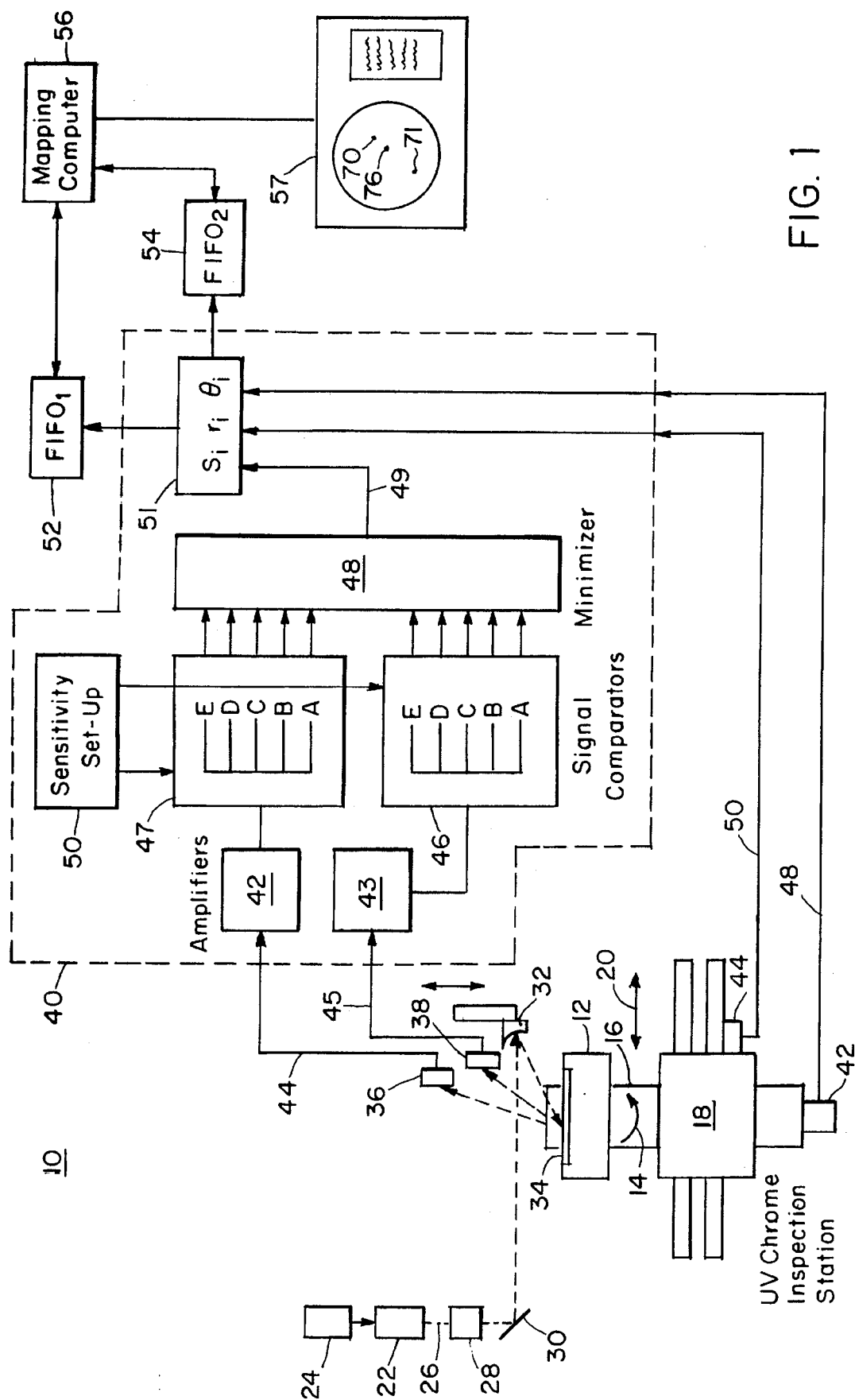
FIG. 1 is a block diagram of a surface inspection apparatus which may incorporate the particle size and position data processing system of this invention.

Inspection system 10, FIG. 1 includes photolithographic mask holder 12 rotated in the direction shown by arrow 14 by air spindle 16 positioned on translation stage 18. Translation stage 18 is equipped with translation encoder 44 to provide information on its position in the direction shown by arrow 20.

Laser 22, powered by power supply 24, delivers laser beam 26 through beam forming optics 28. Beam 26 is directed by mirror 30 to parabolic mirror 32 which focuses it on the surface of photolithographic mask 34. Scattering of the laser beam off the surface is detected by sensors 36 and 38. The output of sensors 36 and 38 is analyzed by processing circuit 40 to deduce the size of a particle or flaw detected on the surface of photolithographic mask 34. The position of a detected flaw or particle is determined based on signals ("counts") from rotation encoder 42 and translational encoder 44.

The size S of a detected particle i is determined as follows. Signal processing circuit subsystem 40 includes amplifiers 42 and 43 responsive to detectors 36 and 38 respectively. Detectors 36 and 38 provide an electrical signal corresponding to the intensity of light detected over lines 44 and 45 to amplifiers 42 and 43 respectively, within analog signal processing circuit 40. The amplified signals are provided to signal comparators banks 46 and 47. Comparators banks 46 and 47 each output a multi-bit digital word to minimizer 48. An absence of a comparator output signal indicates that none of the detectors 36 or 38 detected an intensity level which above a set threshold level. Signals that exceed the threshold level produce different digital words that correspond to the size of the signal and hence the size of the flaw detected. In this example, only five different flaw sizes (A–E) are shown, however, a greater number of sizes could be used. Sensitivity set-up circuit 50 enables the adjustment of the levels A–E so that an operator can vary the sensitivity level for different applications. The digital words corresponding to the signals detected from comparators banks 46 and 47 are provided to minimizer 48 which outputs the minimum intensity level (A–E) detected by detectors 36 and 38. If the minimum detected intensity level from minimizer 48 is equal to zero, this indicates that no defect or only a surface pattern was detected at that particular point on plate 34. If the minimum detected energy level exceeds zero, this indicates that a flaw is present. The levels of intensity A–E are indicative of the size of a given particle. If the intensity level on line 44 from detector 36 is level D, comparator 47 will output a D signal but if the level on line 45 from detector 38 is a level E as output by comparator 46, minimizer 48 will only present size data "D" on line 49.

Figure 2:
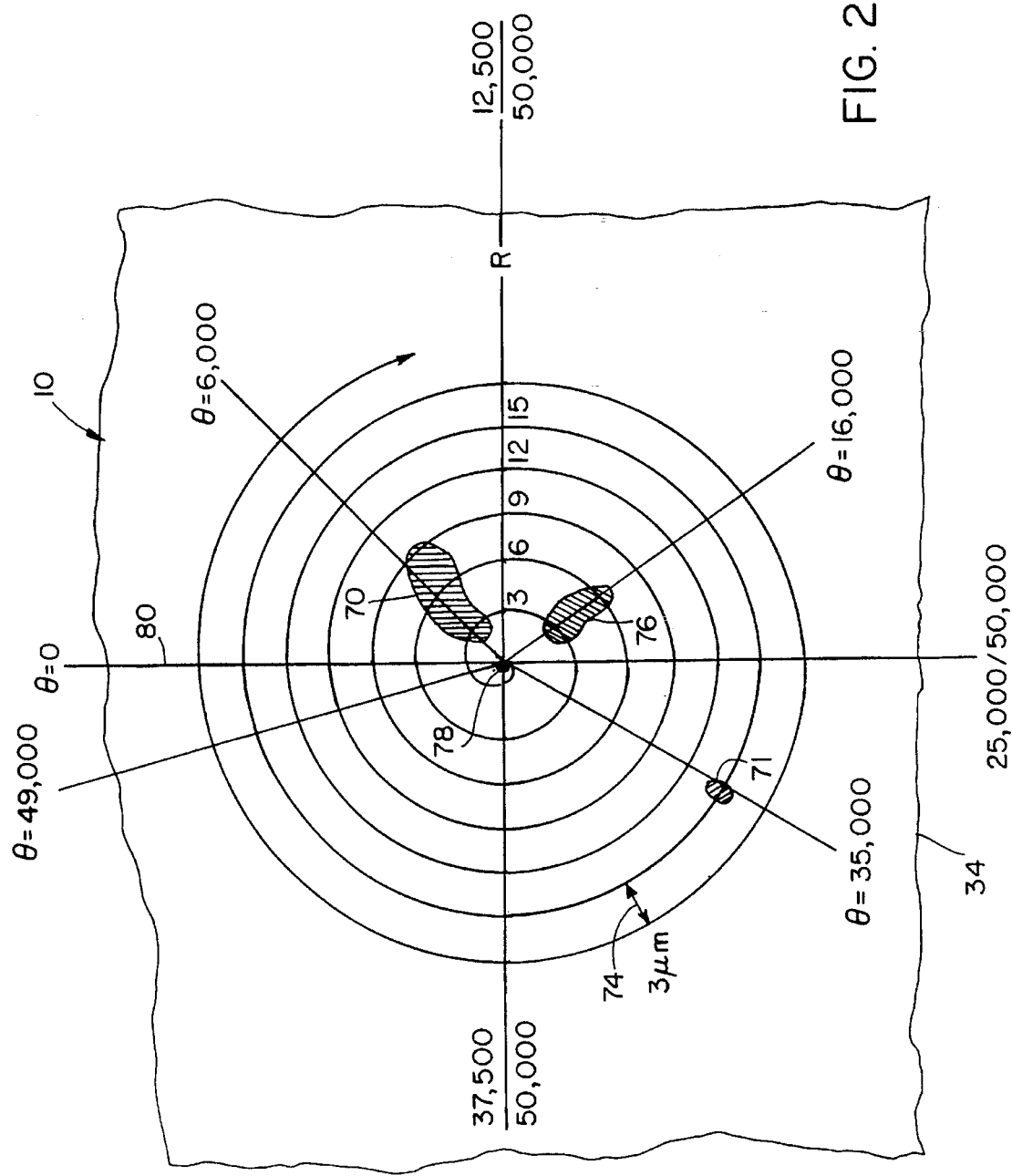
FIG. 2 is a top view of a portion of a typical surface inspected by the surface inspection apparatus of FIG. 1.

The result on line 49 is a signal $S_i$ indicative of a size of a detected particle. The angular position θ of a detected particle i is delivered as signal $θ_i$ from rotational encoder 42 on line 48. The radial position r of a detected particle i is provided as a signal $r_i$ on line 50 from translation encoder 44. One air spindle revolution is divided into 50,000 angular θ data points. Signal processor 40 keeps track of the current angular θ position of spindle 16 using rotary encoder 42 pulses (ticks) which generates an interrupt signal at every index position. In this way, the size (S) and position (r and θ) of particle 70, FIG. 2 is processed. See also U.S. Pat. Nos. 4,943,734; 4,794,264; 4,794,265; and/or 5,389,794.

Unique to this invention are FIFO memories 52 and 54, FIG. 1, which store the size (S) and position (r, θ) data of any detected particles and mapping computer 56 which reads the stored data once per M number of revolutions of photolithographic mask 34.

As shown in FIG. 2, the laser beam trace on the surface of photolithographic mask 34 forms the spiral pattern as shown at 72 with only a 3 micron spacing between heaters of adjacent traces as shown at 74. Beam spot size on the surface is on the order of 10 micrometer at $1/e^2$ intensity level, so the trace overlap at 3 micrometer pitch occurs at approximately 80% intensity level. In this circumstances, a particle can be detected during several subsequent revolutions, of which one revolution will be the most optimal, namely when the beam's most intensive center passes closets to the particle. During adjacent revolutions, the particle will be exposed to lower intensity of light at the beam's periphery, so that its scattering and thus apparent size classification will be diminished.

Mask 34 is divided into 50,000 angular sectors. Therefore, particle 70 may be detected during 4 revolutions, corresponding to radial distances of 3 micrometer (as size "B"), 6 micrometer (as size "D"), 9 micrometer (as size "E") and 12 micrometer, all of them at angular position of 6,000 counts (corresponding to [6,000/50,000]*360°) from reference sector 80.

Particle 76 may be detected at 3 revolutions corresponding to 9 micrometers (size C), 12 micrometers (size B) and 15 micrometers (size B), all at angular position of 16,000. Particle 71 may be detected in one revolution only, as size B at 12 micrometer and θ=35,000.

For the most of final mapping and/or microscope examination of these particles, the above described radial resolution of 3 micrometer is excessive. Accordingly, in this example, the traces at 3, 6, 9, 12 and 15 micrometers are "combined" into one trace for the three particles 70, 76 and 71 at angular position of 6000, 16000 and 35000, respectively particle 71 of size B may be 0.4 micrometer in diameter, particle 75 of size C—0.5 micrometer, particle 70 of size E—1.0 micrometer in diameter.

Accordingly, in this invention, FIFO memories 52 and 54, FIG. 1 are programmed by the signal processing circuit to be updated only if the size data for a particle detected in a given angular sector increases between subsequent revolutions of mask 34. Also, as explained supra, mapping computer 56 automatically switches between FIFO memory 52 and FIFO memory 54 so one can be recording data while the second is transferring data permanent memory.

Figure 3:
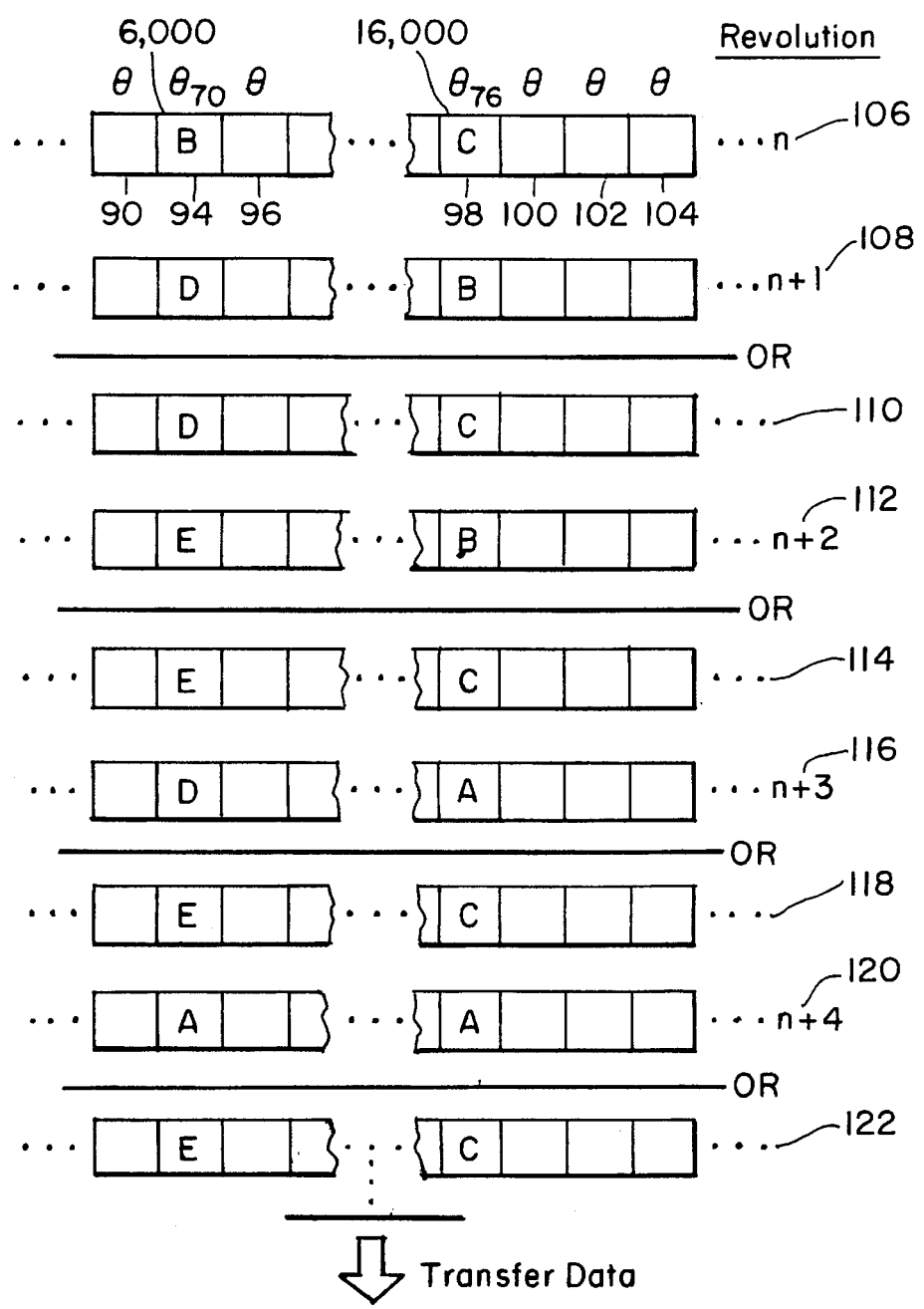
FIG. 3 is a schematic view of a portion of one FIFO memory of the data processing system of this invention.

As shown in FIG. 3, address spaces 90, 94, 96, 98, 100, 102, and 104 are depicted for FIFO memory 52, FIG. 1. There are actually 50,000 such address spaces in each FIFO memory, one for every angular sector partition of surface 34 which can vary depending on the rotational encoder used and the precision of the translation stage incorporated in conjunction with air spindle 16 of system 10, FIG. 1. The size (A–E) of a detected particle is analyzed by processing circuit 40, FIG. 1 which alternatively transmits the size ($S_i$) and position ($r_i$, $θ_i$) data to memories 52 and 54 under the control of computer 56.

Address space 94, FIG. 3, is allocated for θ=6000 and on the first revolution of surface 34 as shown at 106 stores size data "B" for particle 70. Address space 98, allocated for θ=16,000 stores size data C for particle 76. On the next revolution, as shown at 108, the incoming particle size data of particle 70 is "D" and this data replaces the previous size data "B" in address space 94 for particle 70 as shown at 110 since a particle of size "D" is larger than a particle of size "B". On the second revolution, the incoming size data of particle 76 is decreasing to a size "B" but since it is normally desirable to analyze only the maximum size of a given particle, the size "B" data is not stored and instead size data "C" remains in address space 98 for particle 76 as shown at 110. This is accomplished by an "OR" operation wherein the FIFO memories are programmed to automatically accept data in a given address space only if the incoming data is larger than the stored size data already in that address space. On the next revolution, as shown at 112, particle 70 is analyzed as a size "E" while particle 76 is only detected to be a size "B" but the FIFO memories again only store the larger of the incoming data as compared to already stored data as shown at 114. On the next revolution, as shown at 116, no particle is detected in the address space representing θ=16000 while the address space representing θ=6000 receives data indicating that particle 70 is a size "B" but the FIFO memory again only accepts the larger of the incoming data and the already stored data as shown at 118. On the next revolution as shown at 120, particles 70 and 76 are no longer detected and so the address spaces representing data at θ=6000 and θ=16000 are not updated as shown at 122. Finally, after a number of revolutions, typically M=5, of surface 34, FIG. 2 the data from FIFO memory, 52, FIG. 1 is transferred to mapping computer 56. The data transferred in this example is that particle 70 is of size E and located at θ=6,000, r=15 um; particle 76 is of size C and located at θ=16,000 r=15 um.

This data is transferred from FIFO memory 52, FIG. 1 while FIFO memory 54 is now used to store size and position data for the next five revolutions of surface 34. Once the size and position data is transferred, mapping computer 56, FIG. 1, provides the user with a picture on display 57 of the position and size (by color coding) of particles 76, 70 and 71 so that quality control personnel can determine whether photolithographic mask 34 is clean enough to be used for a production run.

This results at a significant savings of processing time since first, the extraneous size data for a given particle was never stored and second, because there are two FIFO memories 52 and 54 and one can be used to store particle size data while the other is read by mapping computer 56.

Figure 4:
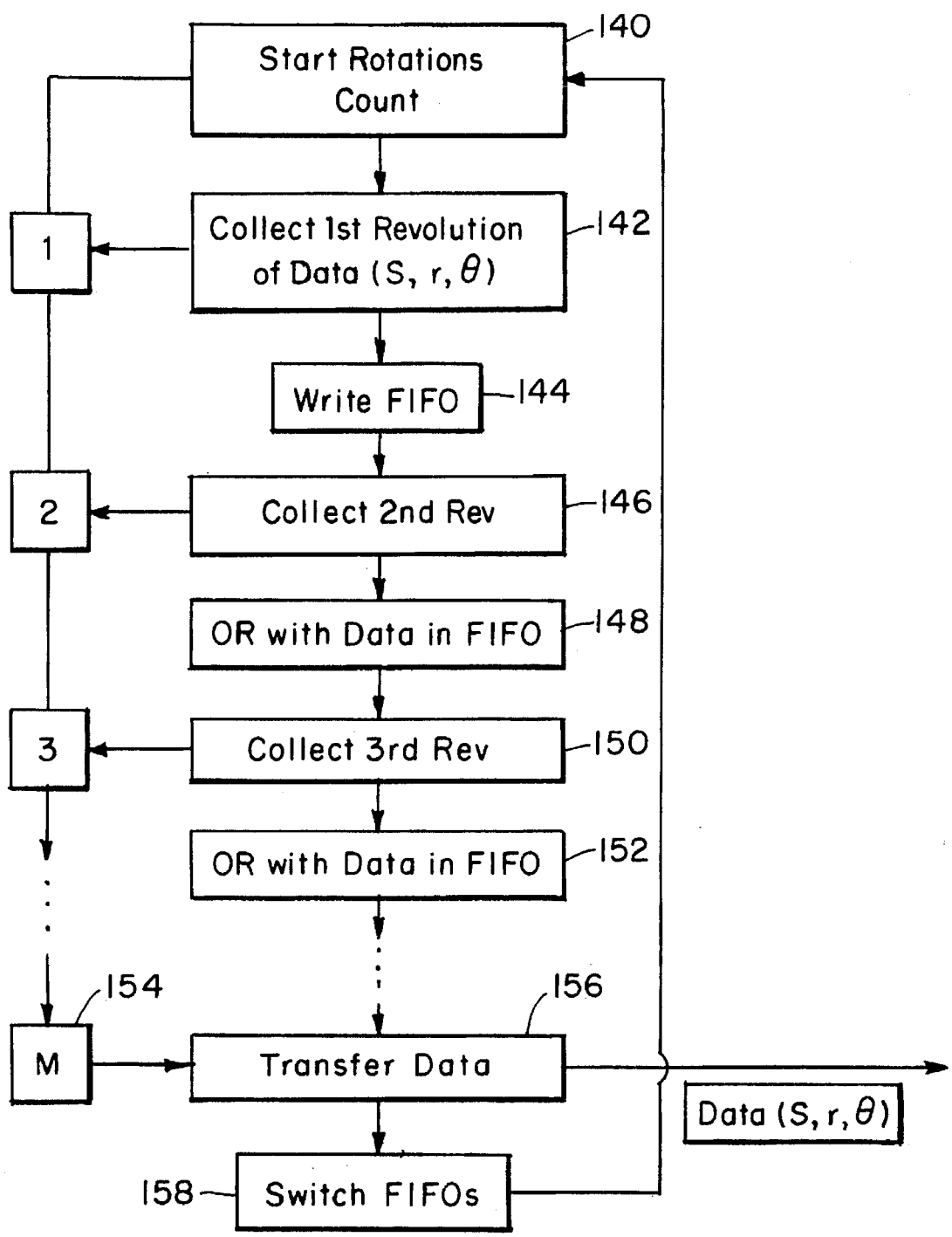
FIG. 4 is a functional flow chart of the data processing routine of this invention.

FIG. 4 is a flow chart of the microscode in signal processing circuit 56, FIG. 1, for achieving the results shown in FIG. 3. In step 140, FIG. 4, the rotation counter is started as shown at 106, FIG. 3 and the size (S) and position (r, Θ) of any particles detected during the first revolution as shown at 106, FIG. 3, is collected, step 142, FIG. 4, and written to one of the FIFO memories, step 144. The size and position data for the next revolution as shown at 108, FIG. 3, is also collected, step 146, FIG. 4, and then as shown at 110 in FIG. 3, "ORed" with the data already in the FIFO memory, step 148, FIG. 4. The size and position data for the next revolution is collected as shown at 112 in FIG. 3, step 150, FIG. 4 and again "ORed" with the data already in the FIFO memory as shown at 114, FIG. 3, step 152, FIG. 4. After a number of M revolutions as shown at 154, the data from that FIFO memory is transferred, step 156, to mapping computer 56, FIG. 1 and the FIFO memories are switched, step 158 and the process starts all over again at steps 140 for the next M revolutions.

M is preferably set to 5 for system 10, FIG. 1, since the microscope used to manually inspect the surface of photolithographic mask 34 after it is automatically inspected by system 10 typically only has a resolution of about 15 microns×15 microns and it takes 5 revolutions of photolithographic mask 34 before the laser beam covers 15 microns in the radial direction.

Using a single memory and capturing the size and position data for each 50,000 ticks of rotational encoder 42, FIG. 1 for each revolution of photolithographic mask 34 would involve a considerable amount of processing time and result in enormous amounts of unusable data since quality control personal are only interested locating defects with resolution of 15×15 um, substantially larger that 3 uu intertrace distance. Any finer resolution as far as particle position information is concerned is not required and slows down processing time thereby slowing down the rate of inspection of a series of photolithographic masks using system 10, FIG. 1. The following is the actual microcode operant in signal processing circuit 56, FIG. 1 to achieve the results shown in FIG. 3;

```
    CLOCK:(CLK,CLK),
    2:RST, 11:GO, 14:INDX, 23:ENC, 3:XFER, 22:ORDATA, 21:F1WR, 20:F2WR,
    19:FWR, 18:WRBNK2, 17:WRBNK1, 16:DRQ, 15:FFRD, 7 . . . 10:STT[3 . . . 0]
    HIGH: GO, INDX, XFER, RST, ORDATA, STT[3 . . 0], FWR
    REGISTERS: CLK // STT[3 . . . 0], WRENK1

{ STATES: START = 0, WAIT1 = 1, WRFIFO1 = 5, WRFIFO2 = 3, READ = 11, WRFIFO3 = 15,
    WAIT2 = 9, WRFIFO4 = 13, SPR2 = 2, SPR4 = R, SPR6 = 6, SPR7 = 7, SPR8 = 8,
    SPR10 = 10, SPR12 = 12, SPR14 = 14

START.                                                          | INITIAL STATE
        DRQ = 0
        RST                              ? → START
        INDX                             ? → WAIT1
                                           → START

WAIT1.                                                          WAIT FOR
        RST                              ? → START                  ENCODER
        ENC & ! INDX                     ? → WRFIFO1                OR INDEX
        INDX                             ? → WRFIFO2                PULSE
        INDX                             ? → WRFIFO4                COLLECT ONLY 0
                                           → WAIT1

WRFIFO1.                                                        WRITE TO FIFO
        RST                              ? → START                  AFTER ENCODER
                                           → WAIT1

WRFIFO2.                                                        WRITE TO FIFO
        RST                              ? → START                  AFTER INDEX
                                           → WAIT2

WAIT2.
        RST                              ? → START
        ORDATA = 1
        ENC & ! (INDX & XFER)            ? → READ
        INDX & XFER                      ? → WRFIFO4
                                           → WAIT2

READ.                                                           WAIT FOR
        RST                              ? → START                  ENCODER OR
        ORDATA = 1                                                  INDEX PULSE
        FFRD    = 1
                                           → WRFIFO3

WRFIFO3.                                                        WRITE TO FIFO
        RST                              ? → START                  AFTER ENCODER
        ORDATA = 1                                                  WHILE "OR-ING"
                                           → WAIT2
```

```
                                            -continued
WRFIFO4.                                                          WRITE TO FIFO
    RST                                    ? → START              AFTER INDEX
    ORDATA = 1                                                    WHILE "OR-ING"
    DRQ = 1                                                       SET "DRQ"
                                             → WAIT1
}                                                                 | BANKS WRBNK1 = ! (STT[3 . . . 0] == 0) & ((!WRBNK1 & (STT[3 . . . 0] == 13)) #
             (WRBNK1 & ! (STT[3 . . . 0] == 13)))
    WRBNK2 = !WRBNK1
    F1WR   = (WRBNK1 & ((STT[3 . . . 0] == 5) # (STT[3 . . . 0] == 15)))
    F2WR   = (!WRBNK1 & ((STT[3 . . . 0] == 5) # (STT[3 . . . 0] == 15)))
    FWR    = F1WR # F2WR
```

Although specific features of the invention are shown in some drawings and not others, however, this is for convenience only as some feature may be combined with any or all of the other features in accordance with the invention.

Other embodiments will occur to those skilled in the art and are within the following claims:

What is claimed is:

1. A surface inspection system comprising:

a laser beam source;

means for focusing a laser beam from said source onto the surface;

means for rotating and translating said surface with respect to said means for focusing to trace a spiral pattern with said laser beam on said surface;

detection means for detecting scattering of said laser beam from the surface;

means, responsive to said detection means, for calculating the size of any detected particles on the surface and for determining the position of said detected particles on the surface;

memory means for storing the size and position data of any detected particles; and means, responsive to said memory means, for recording said size and position data of any detected particles in said memory means on each revolution but transferring said stored data out of said memory means once per M revolutions.

2. The system of claim 1 further including means for recording size data in said memory means each revolution for M revolution only if the incoming size data for a detected particle is larger than the stored size data for that particle.

3. The system of claim 2 in which said memory means includes two FIFO memories, one recording data while the second is transferring data and means for switching between said memories every M revolutions.

4. The system of claim 3 in which said FIFO memories are programmed to receive data only if the incoming size data for an address space is greater than the size data stored in said address space.

5. A data processing system for a surface inspection apparatus which analyzes flaws by size and position on a surface, the data processing system comprising:

means for obtaining flaw size and position data from the surface inspection apparatus;

first and second memories;

means for recording size data in one memory while transferring size data from the second memory and switching memories every M revolutions of the surface; and means for replacing a stored size datum for a given position in one of said memories during each revolution for M revolutions with an incoming size datum only if the incoming size datum is greater than the stored size datum.

6. A data processing system comprising:

means for counting;

means for obtaining data;

first and second memories;

means for recording said data in said first memory while reading data from said second memory and switching memories after every M counts; and means for replacing previously stored data in an address space of one of said first and second memories with incoming data only if the incoming data meets a preselected criteria.

7. The data processing system of claim 6 in which said preselected criteria is that the incoming data must be greater than the stored data.

8. A data processing system for a surface inspection apparatus, the data processing system comprising:

first and second memories;

means for obtaining flaw size and position data;

means for writing size data to said first memory while reading size data from said second memory and switching memories every M revolutions of the surface; and means for replacing stored size data for a given position during each revolution for M revolutions with incoming size data only if the incoming size data is greater than the stored size data.

9. A system for processing particle size and position data for a surface under inspection, the system comprising:

means for rotating and translating a surface with respect to a beam of radiation used to detect particles on the surface;

means for dividing the surface into a number N of angular vectors;

means for counting the number of revolutions of the surface;

means for collecting particle size and position data at each angular vector during each revolution;

first and second memories having at least N address spaces, each address space allocated for a specific angular vector;

means for recording the collected particle size and position data in the first memory while transferring particle size and position data from the second memory and switching memories every M revolutions; and means for storing in each said address space of said memories the greater of stored size data and incoming size data.

10. A data processing method for a surface inspection apparatus which analyzes flaws by size and position on a surface, the data processing method comprising:

obtaining flaw size and position data from the surface inspection apparatus;

writing size data to one memory while reading size data from a second memory and switching memories every M revolutions of the surface; and replacing a stored size datum for a given position in a memory during each revolution for M revolutions with an incoming size datum only if the incoming size datum is greater than the stored size datum.

11. A data processing method comprising:

obtaining flaw size and position data;

writing said data to one memory while reading data from a second memory and switching memories after every M counts; and replacing previously stored data in an address space of a memory with incoming data only if the incoming data meets a preselected criteria.

12. The data processing method of claim 11 in which said preselected criteria is that the incoming data must be greater than the stored data.

13. A data processing method for a surface inspection apparatus, the data processing method comprising:

obtaining flaw size and position data;

writing size data to one memory while reading size data from a second memory and switching memories every M revolutions of the surface; and replacing stored size data for a given position during each revolution for M revolutions with incoming size data only if the incoming size data is greater than the stored size data.

14. A method of processing particle size and position data of particles detected on a surface under inspection, the method comprising:

rotating and translating a surface with respect to a beam of radiation used to detect particles on the surface;

dividing the surface into a number N of angular vectors;

counting the number of revolutions of the surface;

collecting flaw size and position data at each angular vector during each revolution;

establishing first and second memories each having at least N address spaces, each address space allocated for a specific angular vector;

writing the collected particle size and position data to the first memory and reading particle size and position data from the second memory and switching memories every M revolutions; and programming said memories to store in each said address space the greater of previously stored size data and incoming size data.

* * * * *